United States Patent [19]  
Nystrom et al.

[11] Patent Number: 4,586,974  
[45] Date of Patent: May 6, 1986

[54] PROCESS OF FORMING AN EXTERNAL MALE CATHETER AND APPLICATOR

[75] Inventors: Wilford O. Nystrom, Mundelein; Kenneth E. Riedel, Naperville; David L. Doerschner, Rolling Meadows, all of Ill.

[73] Assignee: Hollister Incorporated, Libertyville, Ill.

[21] Appl. No.: 726,677

[22] Filed: Apr. 24, 1985

Related U.S. Application Data

[62] Division of Ser. No. 510,904, Jul. 5, 1983, Pat. No. 4,540,409.

[51] Int. Cl.⁴ .......................... A61F 5/44; B32B 31/00
[52] U.S. Cl. .................... 156/165; 156/229; 427/171
[58] Field of Search .............. 156/165, 229, 291, 247, 156/240, 203, 204; 427/171; 604/349, 352

[56] References Cited

U.S. PATENT DOCUMENTS

| 3,336,926 | 8/1967 | Srosham | 604/349 |
| 3,339,551 | 9/1967 | Stoutenburgh | 128/295 |
| 3,353,538 | 11/1967 | Carrigan | 128/295 |
| 3,364,932 | 1/1968 | Beach | 128/295 |
| 3,405,714 | 10/1968 | Moss | 128/295 |
| 3,421,507 | 1/1969 | Srosham | 604/349 |
| 3,511,241 | 5/1970 | Lee | 128/295 |
| 3,631,857 | 1/1972 | Maddison | 128/295 |
| 3,721,243 | 3/1973 | Hesterman | 128/295 |
| 3,742,953 | 7/1973 | Lee | 128/295 |
| 3,788,324 | 1/1974 | Lim | 128/295 |
| 4,022,213 | 5/1977 | Stein | 128/295 |
| 4,187,851 | 2/1980 | Hauser | 128/295 |
| 4,239,044 | 12/1980 | Pavlinch | 128/295 |
| 4,284,079 | 8/1981 | Adair | 128/295 |
| 4,296,502 | 10/1981 | Bortle | 4/144.1 |
| 4,378,018 | 3/1983 | Alexander | 128/295 |

FOREIGN PATENT DOCUMENTS 162302 8/1952 Sweden .

Primary Examiner—Michael Ball  
Attorney, Agent, or Firm—Tilton, Fallon, Lungmus

[57] ABSTRACT

An external male urinary drainage catheter combined with a tubular applicator for applying and adhesively securing the catheter to a user. The method of use of the applicator/catheter combination, and the method of adhesively coating the inner surface of the catheter sheath during manufacture, are also disclosed.

6 Claims, 8 Drawing Figures

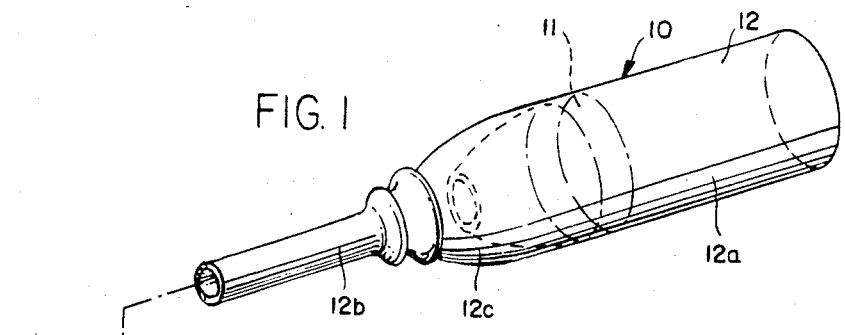
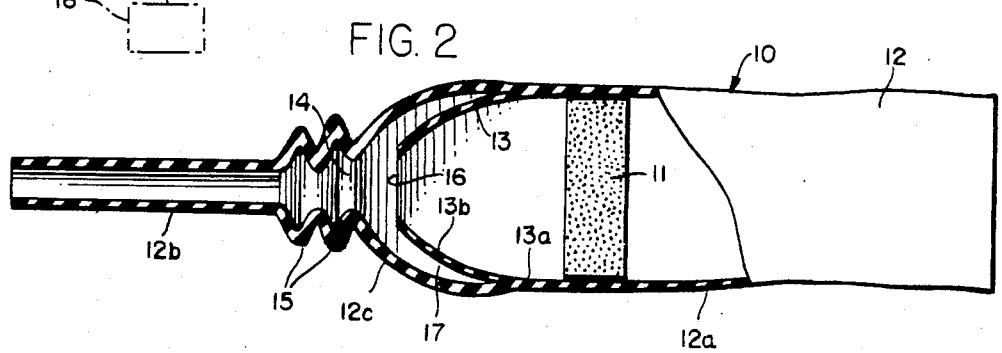
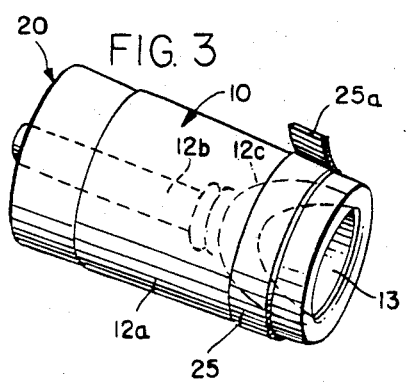
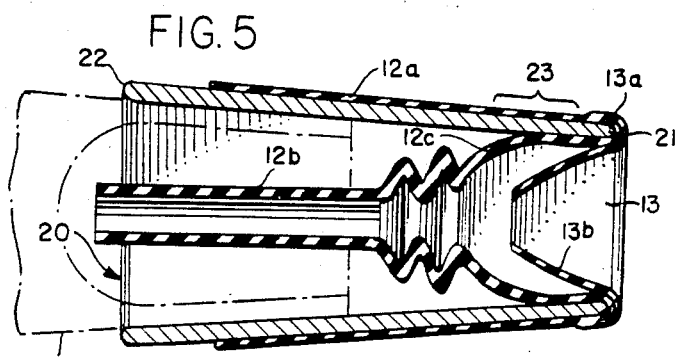
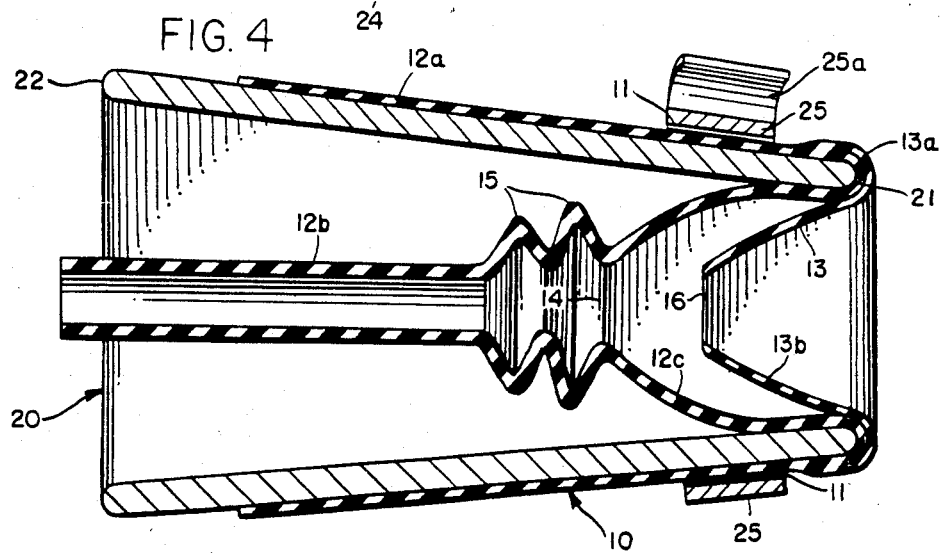

PROCESS OF FORMING AN EXTERNAL MALE CATHETER AND APPLICATOR

This application is a division of application Ser. No. 510,904, filed July 5, 1983, now U.S. Pat. No. 4,540,409.

BACKGROUND

The use of external catheters for male urinary drainage systems is well known, as disclosed in U.S. Pat. Nos. 4,378,018, 4,187,851, 3,863,638 and 3,835,857. Essentially such a system comprises an elastic sheath adapted to fit over the user's penis, the sheath having an outlet at its distal end connected to a tube leading to a suitable collection receptacle. Since leakage resulting from fluid backflow between the penis and sheath is clearly undesirable, it has become a common practice to interpose a sealant pad between the sheath and the penile shaft as disclosed, for example, in U.S. Pat. No. 4,187,851 and in co-owned U.S. Pat. No. 4,378,018.

While a sealant pad, when properly used, performs the dual functions of preventing leakage and retaining the catheter in place, difficulties have been reported in fitting such pads and catheters upon users exactly as intended. For example, a pad of the type depicted in U.S. Pat. No. 4,187,851 takes the form of an adhesive strip intended to be wrapped about the penile shaft before the elastic catheter is unrolled into position over the penis. Performing such operations may be difficult or impossible by patients suffering from urinary incontinence since such patients often lack the motor control and/or mental acuity necessary for such manipulations. Nurses or other attendants may be unable to take the time necessary for properly wrapping and molding the sealant pads in place, and for then carefully fitting the sheaths over the pads to form leakproof seals. Should errors be made that might increase the possibilities of subsequent leakage, a nurse or attendant might nevertheless leave the improperly-applied pad and catheter in place because of time constraints or because of patient discomfort that might be associated with removing the improperly-applied pads and starting over. Moreover, problems resulting from improper application of an appliance might be more serious than occasional fluid leakage or mild patient discomfort. Thus, should an adhesive pad of the type shown in U.S. Pat. No. 4,187,851 be wrapped too tightly about the penile shaft, circulation might be impaired and tissue necrosis could result.

External catheters are currently available that are internally coated with pressure-sensitive adhesive and therefore eliminate the need for using separate adhesive-coated sealant pads. While such a construction avoids some of the more serious dangers associated with wrap-around sealant pads, the difficulties of application, and the problems of leakage resulting from improper application, persist and may even be more pronounced. Considerable care must be taken when unrolling an adhesive-coated sheath over the penis to make certain that the sheath is evenly applied without developing wrinkles and flow channels. All too frequently the adhesive-coated inner surfaces of such a sheath come into contact with each other during application of the catheter. Separation of the contacting surfaces, if possible at all, is difficult and time-consuming, with the result that corrective steps may not be taken and leakage of the catheter in later use is practically assured.

Other prior patents of general interest are Swedish patent No. 162,302 and U.S. Pat. Nos. 4,022,213, 4,284,079, 3,405,714, 4,239,044, 3,353,538, 3,511,241, 3,721,243, 3,631,857, 3,788,324, 3,339,551, 3,364,932, 4,296,502, and 3,742,953.

SUMMARY OF THE INVENTION

This invention is concerned broadly with a combination of an external male catheter and a tubular applicator for greatly simplifying and expediting the procedure for effectively applying the catheter to the penis, especially where such catheter has its internal surface coated with a pressure-sensitive adhesive. In a preferred embodiment, the catheter has an integral inner sleeve adapted to engage the glans of the penis and provide an expandable space between the inner sleeve and the distal end of the outer sheath to accommodate surges of fluid at the commencement of urination. The applicator coacts with such a catheter to facilitate proper orientation of the inner sleeve in relation to the glans at the time the catheter is fitted in place. Further aspects of the invention relate to the method for facilitating the attachment of an adhesive-coated external catheter to the penis of a patient utilizing a tubular catheter support, and to the method of utilizing the applicator tube not only during the application of such a catheter to a patient but also during the step of product manufacture when the pressure-sensitive adhesive is applied to the catheter.

Briefly, the combination takes the form of an applicator tube supporting an external male urinary catheter with its distal portion disposed within the tube and its cylindrical body portion everted and extending externally about the tube. Specifically, the open-ended applicator tube has a length substantially less than that of the catheter as a whole and has an outside diameter slightly greater than the maximum inside diameter of the elastic catheter in its unstretched state. The distal portion of the catheter, which includes the catheter's neck portion and outlet section, is axially disposed within the open-ended application tube. The proximal portion of the catheter, which takes the form of an elongated cylindrical portion, projects from the entrance opening of the tube and is reversely turned about the tube's outer surface to expose the adhesive coating of the cylindrical portion's everted and normally inner surface.

The outlet or drainage section of the catheter is accessible from and preferably projects through the opening at the opposite end of the applicator tube. By gripping the outlet section and moving the tube in the opposite direction away from that section, the everted cylindrical portion of the catheter disposed externally of the tube slides back into the tube and, in so doing, is reverted or restored to a normal condition in which the adhesive-coated inner surface faces inwardly. Therefore, if the glans of the penis is first placed within the entrance of the tube, and the tube is then advanced over the penis at the same time that the catheter's drainage tube section is restrained or even pulled slightly in the opposite direction, causing the catheter's cylindrical portion to slide into reverted condition within the applicator tube, the catheter sheath will ultimately assume a position about the penis with its adhesive inner surface engaging the penile shaft directly behind (proximal to) the corona of the glans.

Ideally the applicator tube is tapered with its entrance opening (about which the catheter is reversely folded) being smaller than the opening at the tube's opposite end. If the catheter is provided with an inner sleeve, as disclosed in co-owned copending application Ser. No. 271,086, filed June 5, 1981, the proximal portion of that sleeve should be exposed at the entrance to the tube and should be folded in a reverse direction about that entrance to insure that the distal end of the sleeve will be positioned for direct contact with the glans of the penis before reversion of the catheter is undertaken. Sliding movement of the catheter during the reverting step is facilitated by incorporating anti-friction means between the everted cylindrical body of the catheter sheath and the applicator tube. Such means may include texturing the tube's outer surface or otherwise reducing the outer surface area of the tube in direct contact with the catheter, and/or by interposing a lubricating material between the tube's outer surface and the everted cylindrical body portion of the catheter.

In addition to functioning as a device for applying an external urinary catheter to a male patient, the applicator tube may function as a mandrel for supporting the catheter prior to and during the step of adhesively coating the cylindrical body portion of the catheter during manufacture of the product. Such adhesive may be applied by any suitable technique such as by spraying, rolling, brushing, etc.; however, a particularly effective method has been found to consist of wrapping the mandrel-supported catheter with a strip of adhesive tape, the tape having a backing to which the adhesive adheres less strongly than to the elastic material of the catheter. The backing of the tape therefore serves as a carrier for applying a band of pressure-sensitive adhesive to the everted cylindrical portions of a catheter supported by the applicator tube, and thereafter functions as a release strip which may be peeled away from the catheter to expose the adhesive coating thereon when the catheter is to be applied to a patient.

Other features, advantages, and objects of the invention will become apparent from the drawings and specification.

DRAWINGS

FIG. 1 is a perspective view of a catheter used in a combination constituting a preferred embodiment of this invention.

FIG. 2 is a longitudinal sectional view of the catheter shown in a normal condition of use and with the protective release sheet removed from the adhesive layer or coating.

FIG. 3 is a perspective view illustrating a preferred embodiment of the catheter/applicator combination as it would appear just prior to use.

FIG. 4 is an enlarged longitudinal sectional view of the combination depicted in FIG. 3.

FIG. 5 is a reduced longitudinal sectional view similar to FIG. 4 but illustrating the catheter as it would be supported in a manufacturing operation during application of the pressure-sensitive adhesive layer or band.

DESCRIPTION OF PREFERRED EMBODIMENT

Figure 6:
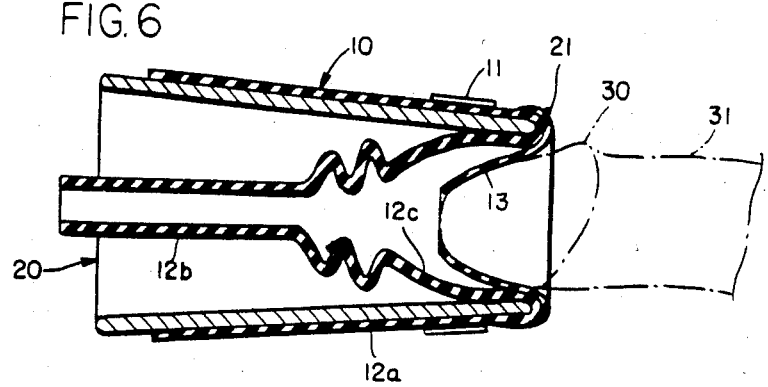
FIGS. 6-8 illustrate successive steps in the application of an external catheter to a male patient using the applicator tube of the catheter/applicator tube combination.

The external male urinary drainage catheter which constitutes one element of the two-element combination of this invention may be an adaptation of a conventional external catheter of the type disclosed, for example, in U.S. Pat. Nos. 4,378,018 (FIG. 7) and 4,187,851 (FIG. 3); however, a catheter having the features disclosed in co-owned copending application Ser. No. 271,086, filed June 5, 1981, is believed particularly desirable because of its inner sleeve construction. The external catheter 10 shown most clearly in FIGS. 1 and 2 is similar (but not identical) to the catheter of such copending application, the main difference being that catheter 10 is internally coated with a band or zone 11 of pressure-sensitive adhesive.

Catheter 10 is formed of soft, highly elastic, natural or synthetic rubber. Natural latex is preferred but other elastomers having similar properties may be used. The catheter includes an elongated outer sheath 12 and an inner sleeve 13, the two being integral or permanently integrated as hereinafter described.

Outer sheath 12 includes an elongated cylindrical section 12a, a reduced drainage tube section 12b, and a tapered neck section 12c disposed therebetween. The wall thickness of the cylindrical section 12a is substantially less than that of the neck and drainage tube sections. For example, the cylindrical section may have a wall thickness within the general range of 0.006 to 0.010 inches and, in general, is too thin or limp to retain a cylindrical configuration without support. In contrast, the wall thicknesses of the drainage tube and neck sections may be 0.050 inches or more and are generally great enough so that such sections will retain the configurations shown in the absence of distorting forces and will spring back into the illustrated shapes when distorting forces are removed.

At its forward or distal end, neck section 12c is provided with a rounded taper leading to a reduced opening 14 (FIG. 2). The drainage tube section 12b that merges with the tapered neck section 12c is provided with a plurality of convolutions or annular enlargements 15. Two such convolutions of graduated size are depicted, their purpose being to permit greater stretchability, bending, and twisting of the drainage tube section when the device is in use, and to do so with less chance that kinking or obstruction of the lumen might occur. Also, since the interior of the drainage tube section is enlarged at such convolutions, convolutions increase the fluid capacity of that section and provide a reservoir for accommodating surges of fluid when the device is in use.

Inner sleeve 13 has a proximal end portion 13a that merges smoothly with the distal end of the sheath's cylindrical body section 12a and an elongated distal end portion 13b disposed within the sheath's neck section 12c. The distal portion 13b tapers forwardly and inwardly, terminating in a reduced distal opening 16 that is spaced well behind (i.e., proximal to) opening 14. The setback also results in the provision of an annular and axially-elongated expansion space 17 between the outer surface of the sleeve's distal end portion 13b and the inner surface of neck section 12c. The wall thickness of the sleeve may be varied but, to insure conformability, good sealing properties, and wearer comfort, such thickness should approximate that of the relatively thin cylindrical body section 12a. Thus, both the cylindrical body section 12a and the inner sleeve 13b should appear as thin, limp, highly stretchable membranes, in contrast to the drainage tube and neck sections 12b and 12c with their shape-retaining properties.

In the preferred embodiment disclosed herein, catheter 10 is also provided with an internal adhesive coating or band 11 (FIG. 2). The adhesive zone is located within the cylindrical section 12a of the sheath behind inner sleeve 13. While the adhesive coating might conceivably extend the full length of the cylindrical section 12a, it is believed preferable to provide the adhesive zone in the form of a narrow but continuous band location within the distal portion of the sheath's cylindrical section 12a. The adhesive coating may be composed of any suitable medical-grade pressure-sensitive adhesive of a type well known in the art; a hypo-allergenic acrylic adhesive is believed to be particularly effective.

Application of the adhesive band to the catheter is undertaken as one of the final steps in the manufacture of the product. The catheter, complete except for the adhesive coating, is fitted upon a support tube 20 as shown in FIG. 5 with the drainage tube section 12b and neck section 12c generally disposed within the tube and the cylindrical body section 12a being everted and extending along the outer surface of the open-ended tube.

The elongated open-ended tube 20 is generally cylindrical in configuration although, as shown in the drawings, the preferred embodiment has a slight but definite taper. A taper within the range of 1 to 4 degrees measured from the longitudinal axis of the tube has been found effective, with a taper of approximately 2 degrees being preferred. The edges at the reduced end or entrance end 21 are rounded (when viewed in longitudinal section) and, if desired, the edges at the opposite end 22 may be similarly formed. Tube 20 may be composed of any of a wide variety of generally stiff materials such as cardboard or relatively rigid plastic materials. A polyolefin such as high density polyethylene is believed particularly suitable, but other polymeric materials having similar properties would also be appropriate.

The length of tube 20 should be substantially less than the length of the catheter as a whole but not less than the length of the sheath's cylindrical section 12a. Ideally, the tube should be substantially longer than the sheath's cylindrical section so that, as shown in FIGS. 3–5, a portion of the tube's larger end is exposed and may be gripped between the fingers during use of the device. The outside diameter of the tube at its entrance end 21 should also be slightly greater than the inside diameter of the cylindrical portion 12a in an unstretched state. As shown in FIGS. 4 and 5, the inside diameter at the entrance end 21 of the tube approximates (or is slightly larger than) the maximum outside diameter of the sheath's neck section 12c in an unstretched state. Of particular importance is the fact that the elongated outlet section or drainage tube section 12b of the catheter terminates at, and preferably slightly beyond, the opening at the opposite end 22 of the supporting tube 20 so that a user may easily grasp the outlet section 12b and pull it outwardly through that opening.

If the catheter 10 is provided with an inner sleeve 13 as described and shown, then it has been found advantageous to mount the catheter upon tube 20 so that the proximal end portion 13a of the sleeve is also everted and is disposed about the outside of tube 20 adjacent entrance 21. The effect is to stretch or enlarge the proximal end of the sleeve and to reduce the length of that portion of the sleeve disposed within tube 20. Because the distal end portion 13b of sleeve 13 is thereby positioned at the entrance 21 of support tube 20, it is exposed in a manner that facilitates fitting the catheter upon a patient when the tube 20 is used as an applicator device as described in detail hereinafter.

With the catheter 10 supported by tube 20 in the manner depicted in FIG. 5, a coating or band of pressure sensitive adhesive may easily be applied to that portion of the stretched cylindrical section 12a indicated by numeral 23. The tube 20 may in turn be supported by a mandrel; one arrangement, with the enlarged end of the tube 20 being fitted upon and frictionally supported by such a mandrel 24, is indicated in phantom in FIG. 5. For purposes of supporting the catheter for application of adhesive to the everted inside surface of that catheter in zone 23, support tube 20 in effect functions as an extension of the mandrel 24.

The adhesive may be applied to the exposed surface of the catheter by spraying, rolling, brushing, or by any other suitable method. A particularly effective method lies in wrapping zone 23 with a strip of pressure-sensitive adhesive tape having an adhesive capable of bonding more tenaciously to the elastomeric material of the catheter than to the backing material of the tape. The backing therefore functions initially as a carrier for transferring the adhesive material to the supported catheter, and then serves as a protective release sheet which later may be stripped away to expose the adhesive coating of the catheter in zone 23.

FIGS. 3 and 4 illustrate the catheter/applicator tube combination as it would appear prior to use by a patient. The adhesive layer 11 extends in a band about the everted inside surface of sheath portion 12a with such adhesive covered by a protective release strip 25. The release strip and adhesive may have been simultaneously applied to the catheter in the manner just described or, alternatively, the adhesive may have been applied in some other manner (as by spraying or rolling) with the protective release strip subsequently wrapped about the adhesive coating to protect that coating until use of the catheter is desired. In any event, some removable protective covering strip 25 should extend over the band 11 of pressure-sensitive adhesive and should be removable to expose that adhesive when use of the catheter is desired. The extension 25a of the covering strip provides a tab portion to facilitate later removal of the protective strip.

The everted cylindrical section 12a of the catheter is retained upon the outer surface of applicator tube 20 primarily because of the stretched condition of the catheter and the recovery force exerted by it. The static frictional forces are weak and are easily overcome by any external forces tending to cause section 12a to slide along the tube 20 in the direction of entrance 21. It is believed apparent that once static frictional forces are overcome there is little to restrain sliding movement of section 12a along the outer surface of the tube 20 because of the diminishing taper of that tube. To help reduce static and dynamic frictional forces, the outer surface of tube 20 may be textured, dimpled, recessed, grooved, apertured, or otherwise treated to reduce the area of direct frictional contact between the tube's outer surface and catheter section 12a. Other means may also be provided for reducing frictional resistance; in particular, talc or some other dry lubricating material may be interposed between tube 20 and catheter section 12a to reduce sliding friction between their opposing surfaces.

In use of the catheter/applicator tube combination, the structure as depicted in FIGS. 3 and 4 is oriented and advanced to direct the glans 30 of penis 31 into the sleeve 13 at the entrance end 21 of the applicator tube 20. The release strip 25 is then peeled away to expose adhesive band 11 although, if desired, the strip may be removed even before insertion of the glans into the interior of sleeve 13. Regardless of the order, when the release strip has been removed and the glans 30 has been inserted into the catheter through the entrance opening of the applicator tube, the parts assume the relationship depicted in FIG. 6.

Figure 7:
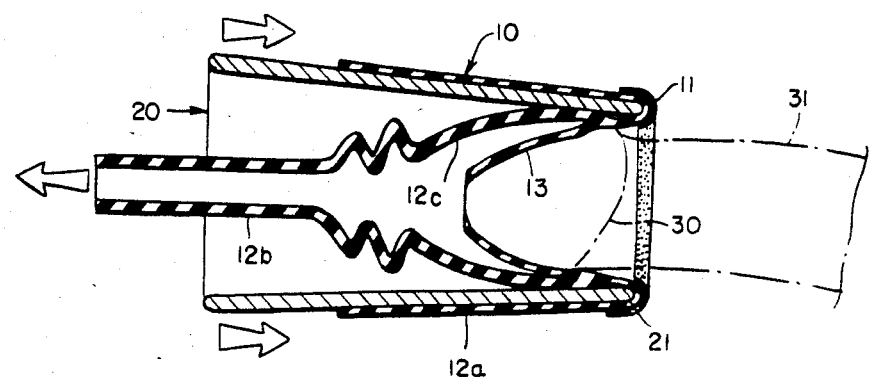
Figure 8:
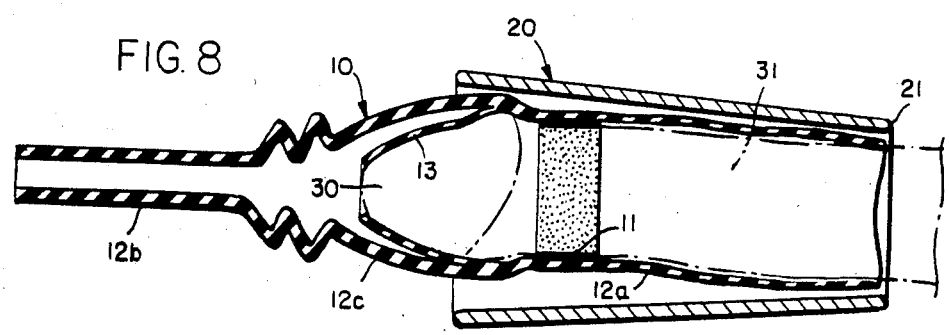

Thereafter, the patient (in the case of self-application), or the nurse or other attendant, grips the outlet tube section 12b adjacent the opening at the enlarged end 22 of the applicator tube and restrains that section, or even exerts a gentle pulling force, while at the same time urging the applicator tube in the direction of the penis. Static friction between the catheter 10 and the applicator tube 20 is thereby broken and the catheter rolls into reverted condition over penis 31 (FIG. 7). It will be noted that the adhesive band 11 turns into contact with the shaft of the penis directly behind (proximal to) the corona of glans 30 to make sealing engagement with the penis and limit any backflow of fluid when the catheter is later used. When the applicator tube 20 has been urged along the penis to completely revert the catheter 10 (FIG. 8), the user simply withdraws the applicator tube and connects the outlet section 12b to a suitable extension tube leading to a collection receptacle 18 (FIG. 1).

It is believed apparent that while applicator tube 20 is particularly useful in fitting an adhesive-coated catheter 10 upon a user, the applicator tube might also be used in applying a catheter without an adhesive coating, as where an adhesive pad of the type disclosed in the cited prior art has previously been applied to the penis. Also, as earlier indicated, catheter 10 with its internal sleeve 13 represents a preferred embodiment; a more conventional catheter lacking the internal sleeve might also be combined with applicator 20 and applied to a wearer in the manner described. Whether the catheter does or does not have an internal sleeve 13, a first step in the application of the catheter would involve inserting the glans 30 into the neck portion 12c of the catheter through the entrance 21 of the applicator tube.

While in the foregoing we have disclosed an embodiment of the invention in considerable detail for purposes of illustration, it will be understood by those skilled in the art that many of these details may be varied without departing from the spirit and scope of the invention.

We claim:

1. A method for adhesively coating the inner surface of an external catheter having a sheath of thin, stretchable, elastic material, said sheath having a generally cylindrical section merging at one end with a tapered neck section terminating in an outlet section of reduced diameter, comprising the steps of inserting the neck and outlet sections of said sheath axially into one end of a relatively rigid open-ended tube and then folding said cylindrical section back along the outer surface of said tube to support said cylindrical section in stretched condition with its inner surface in everted and exposed condition, and then applying a layer of pressure-sensitive adhesive to the exposed inner surface of the everted cylindrical section supported by said tube.

2. The method of claim 1 in which said tube is supported upon a mandrel during said applying step.

3. The method of claim 1 in which said layer of pressure-sensitive adhesive is applied circumferentially about said cylindrical section in a band having a width narrower than the length of said cylindrical section.

4. The method of claims 1 or 3 in which there is the step of covering said layer of pressure-sensitive adhesive with a removable release, strip.

5. The method of claim 4 in which said removable release strip and said layer of pressure-sensitive adhesive are simultaneously applied to said cylindrical section.

6. The method of claim 5 in which said release strip constitutes a carrier strip for applying said pressure-sensitive adhesive layer to said cylindrical section.

* * * * *